United States Patent
Honda et al.

(10) Patent No.: US 10,342,596 B2
(45) Date of Patent: Jul. 9, 2019

(54) LIVING TISSUE BONDING SYSTEM, TREATMENT INSTRUMENT CONTROL APPARATUS, AND OPERATION METHOD OF LIVING TISSUE BONDING SYSTEM

(71) Applicant: OLYMPUS CORPORATION, Tokyo (JP)

(72) Inventors: Yoshitaka Honda, Hachioji (JP); Takashi Irisawa, Hachioji (JP); Kazue Tanaka, Sagamihara (JP); Sadayoshi Takami, Hachioji (JP); Toshifumi Katsuragi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/979,715

(22) Filed: Dec. 28, 2015

(65) Prior Publication Data
US 2016/0106492 A1    Apr. 21, 2016

Related U.S. Application Data

(63) Continuation of application No. PCT/JP2014/070349, filed on Aug. 1, 2014.

(Continued)

(51) Int. Cl.
*A61B 18/08* (2006.01)
*A61B 18/10* (2006.01)
(Continued)

(52) U.S. Cl.
CPC .......... *A61B 18/085* (2013.01); *A61B 18/10* (2013.01); *A61B 18/1206* (2013.01);
(Continued)

(58) Field of Classification Search
CPC .......... A61B 2018/00636; A61B 2018/00642; A61B 2018/00682; A61B 2018/00702;
(Continued)

(56) References Cited

U.S. PATENT DOCUMENTS 5,702,386 A * 12/1997 Stern .................... A61B 18/00
                                                        606/31
5,735,846 A     4/1998 Panescu et al.
(Continued)

FOREIGN PATENT DOCUMENTS

CN     102665585 A     9/2012
JP     2006-068545 A   3/2006
(Continued)

OTHER PUBLICATIONS

Dec. 22, 2016 Search Report issued in European Patent Application No. 14832700.0.
(Continued)

*Primary Examiner* — Eun Hwa Kim
(74) *Attorney, Agent, or Firm* — Oliff PLC

(57) ABSTRACT

A living tissue bonding system includes a treatment instrument having a heating element which applies thermal energy to living tissue, an element temperature measuring section configured to measure an element temperature T1 of the heating element, a power source configured to generate power, a first calculating section configured to estimate a temperature difference ΔT between the element temperature T1 and a temperature T2 of the living tissue using a table or an equation stored beforehand in order to estimate the temperature difference ΔT based on an output value of the power source, a second calculating section configured to estimate the tissue temperature T2 from the element temperature T1 and the temperature difference ΔT estimated by the first calculating section, and a control section configured
(Continued)

to control the power source based on the tissue temperature T2 estimated by the second calculating section.

14 Claims, 11 Drawing Sheets

Related U.S. Application Data

(60) Provisional application No. 61/861,683, filed on Aug. 2, 2013.

(51) Int. Cl.
*A61B 18/12* (2006.01)
*A61B 18/14* (2006.01)
*A61B 18/00* (2006.01)
*A61B 17/00* (2006.01)
*A61B 18/20* (2006.01)
*A61B 17/11* (2006.01)

(52) U.S. Cl.
CPC ....... *A61B 18/1442* (2013.01); *A61B 17/1114* (2013.01); *A61B 18/20* (2013.01); *A61B 2017/00084* (2013.01); *A61B 2018/00684* (2013.01); *A61B 2018/00702* (2013.01); *A61B 2018/00714* (2013.01); *A61B 2018/00791* (2013.01)

(58) Field of Classification Search
CPC ........... A61B 2018/00714; A61B 2018/00791; A61B 2018/00815; A61B 2018/00821; A61B 2018/00803
See application file for complete search history.

(56) References Cited

U.S. PATENT DOCUMENTS

| | | | |
|---|---|---|---|
| 5,769,847 A | 6/1998 | Panescu et al. | |
| 5,906,614 A | 5/1999 | Stern et al. | |
| 6,162,184 A | 12/2000 | Swanson et al. | |
| 6,293,943 B1 * | 9/2001 | Panescu | A61B 18/1206 606/27 |
| 2003/0055419 A1 | 3/2003 | Panescu et al. | |
| 2005/0222556 A1 | 10/2005 | Ariura et al. | |
| 2009/0076506 A1 | 3/2009 | Baker | |
| 2009/0171342 A1 * | 7/2009 | Klimovitch | A61B 18/1206 606/34 |
| 2009/0248002 A1 | 10/2009 | Takashino et al. | |
| 2011/0087212 A1 | 4/2011 | Aldridge et al. | |
| 2013/0019060 A1 | 1/2013 | Wilkens et al. | |
| 2013/0338659 A1 | 12/2013 | Honda et al. | |
| 2014/0012155 A1 | 1/2014 | Flaherty et al. | |

FOREIGN PATENT DOCUMENTS

| | | |
|---|---|---|
| JP | 5425344 B2 | 2/2014 |
| JP | 2014-508547 A | 4/2014 |
| WO | 96/00036 A1 | 1/1996 |
| WO | 96/00039 A1 | 1/1996 |
| WO | 96/00043 A1 | 1/1996 |
| WO | 96/34569 A1 | 11/1996 |
| WO | 03/020339 A2 | 3/2003 |
| WO | 2012/071388 A2 | 5/2012 |
| WO | 2013/088893 A1 | 6/2013 |
| WO | 2013/094326 A1 | 6/2013 |

OTHER PUBLICATIONS

Sep. 9, 2014 International Search Report issued in International Patent Application No. PCT/JP2014/070349.

Jun. 3, 2015 Office Action issued in Japanese Patent Application No. 2015-516316.

Mar. 31, 2017 Office Action issued in Chinese Patent Application No. 201480035169.9.

Feb. 7, 2018 Office Action issued in European Patent Application No. 14832700.0.

\* cited by examiner

US 10,342,596 B2

LIVING TISSUE BONDING SYSTEM, TREATMENT INSTRUMENT CONTROL APPARATUS, AND OPERATION METHOD OF LIVING TISSUE BONDING SYSTEM

CROSS REFERENCE TO RELATED APPLICATION

This application is a continuation application of PCT/JP2014/070349 filed on Aug. 1, 2014 and claims benefit of U.S. Provisional Patent Application No. 61/861,683 filed in the U.S.A. on Aug. 2, 2013, the entire contents of which are incorporated herein by this reference.

BACKGROUND OF THE INVENTION

1. Field of the Invention

An embodiment of the present invention relates to a living tissue bonding system which applies treatment energy to biological tissue, a treatment instrument control apparatus, and an operation method of the living tissue bonding system.

2. Description of the Related Art

U.S. Patent Application Publication No. 2009/076506 discloses a living tissue bonding system including a pair of clamping sections that apply high frequency power energy and thermal energy to a clamped body to be treated, a high frequency power source that outputs high frequency power for applying the high frequency power energy, a power source for heat generation that outputs heat generation power for applying the thermal energy, and a control section configured to control the high frequency power source and the power source for the heat generation in order to switch high frequency power energy application and application of the thermal energy.

Also, U.S. Patent Application Publication No. 2009/0248002 discloses a living tissue bonding system that applies high frequency power energy to a body to be treated, and applies thermal energy after the application of the high frequency power energy is ended. The high frequency power energy has a function of, by destroying cell membranes of the body to be treated, releasing intracellular components including polymer compounds typified by proteins and integrating the intracellular components with extracellular components typified by collagen. Then, the body to be treated is bonded by the application of the thermal energy.

U.S. Patent Application Publication No. 2013/19060 discloses a living tissue bonding system that applies ultrasound energy and high frequency power energy to a body to be treated.

U.S. Patent Application Publication No. 2005/222556 discloses a living tissue bonding system that applies light energy to a body to be treated using a laser.

That is, a treatment section of a medical treatment instrument applies at least one of thermal energy, ultrasound energy, light energy and high frequency power energy to a body to be treated, as treatment energy.

Here, in order for a living tissue bonding system to obtain an excellent treatment result, it is preferable to control an energy amount based on a temperature of living tissue that is being treated. However, it is not easy to detect a living tissue temperature during treatment. Therefore, in a conventional living tissue bonding system, control is performed based on a temperature of an energy output section, a heating element for example, which is easy to detect, instead of the living tissue temperature.

SUMMARY OF THE INVENTION

A living tissue bonding system of an embodiment includes: a clamping section configured to clamp living tissue; a power source configured to generate treatment energy for bonding the living tissue clamped by the clamping section; an output section provided on the clamping section and configured to output the treatment energy to the living tissue; a temperature measuring section configured to measure a temperature of the output section; a first calculating section configured to use a table or an equation stored beforehand and indicating a correlation between a temperature difference between the temperature of the output section measured in the temperature measuring section and a temperature of the living tissue clamped by the clamping section and an output value outputted from the power source to the clamping section, and to estimate the temperature difference from the table or the equation based on the output value of the power source according to an application time period of the treatment energy; a second calculating section configured to estimate the temperature of the living tissue from the temperature of the output section measured by the temperature measuring section and the temperature difference estimated by the first calculating section; and a control section configured to control the power source based on the temperature of the living tissue estimated by the second calculating section.

A treatment instrument control apparatus of a different embodiment is a treatment instrument control apparatus configured to control treatment energy for living tissue to a clamping section configured to clamp the living tissue, and includes: a power source configured to generate the treatment energy for bonding the living tissue clamped by the clamping section; an output section provided on the clamping section and configured to output the treatment energy to the living tissue; a temperature measuring section configured to measure a temperature of the output section; a first calculating section configured to use a table or an equation stored beforehand and indicating a correlation between a temperature difference between the temperature of the output section measured in the temperature measuring section and a temperature of the living tissue clamped by the clamping section and an output value outputted from the power source to the clamping section, and to estimate the temperature difference from the table or the equation based on the output value from the power source according to an application time period of the treatment energy; a second calculating section configured to estimate the temperature of the living tissue from the temperature of the output section measured by the temperature measuring section and the temperature difference estimated by the first calculating section; and a control section configured to control the power source which generates power for the treatment energy, based on the temperature of the living tissue estimated by the second calculating section.

An operation method of a living tissue bonding system of a different embodiment includes: a step in which an output section provided on a clamping section outputs treatment energy by a power source generating the treatment energy for bonding living tissue clamped by the clamping section; a step in which a temperature measuring section measures a temperature of the output section; a step in which, using a table or an equation stored beforehand and indicating a correlation between a temperature difference between the temperature of the output section measured in the temperature measuring section and a temperature of the living tissue clamped by the clamping section and an output value outputted from the power source to the clamping section, a first calculation section estimates the temperature difference obtained from the table or the equation based on the output value from the power source according to an application time period of the treatment energy; a step in which a second calculating section estimates the temperature of the living tissue from the temperature of the output section measured by the temperature measuring section and the temperature difference estimated by the first calculating section; and a step in which a control section controls the power source based on the temperature of the living tissue estimated by the second calculating section.

According to embodiments of the present invention, a living tissue bonding system with which appropriate treatment is easily performed, a treatment instrument control apparatus with which appropriate treatment is easily performed, and an operation method of the living tissue bonding system with which appropriate treatment is easily performed can be provided.

DETAILED DESCRIPTION OF THE PREFERRED EMBODIMENTS

First Embodiment

<Configuration of Living Tissue Bonding System>

Figure 1:
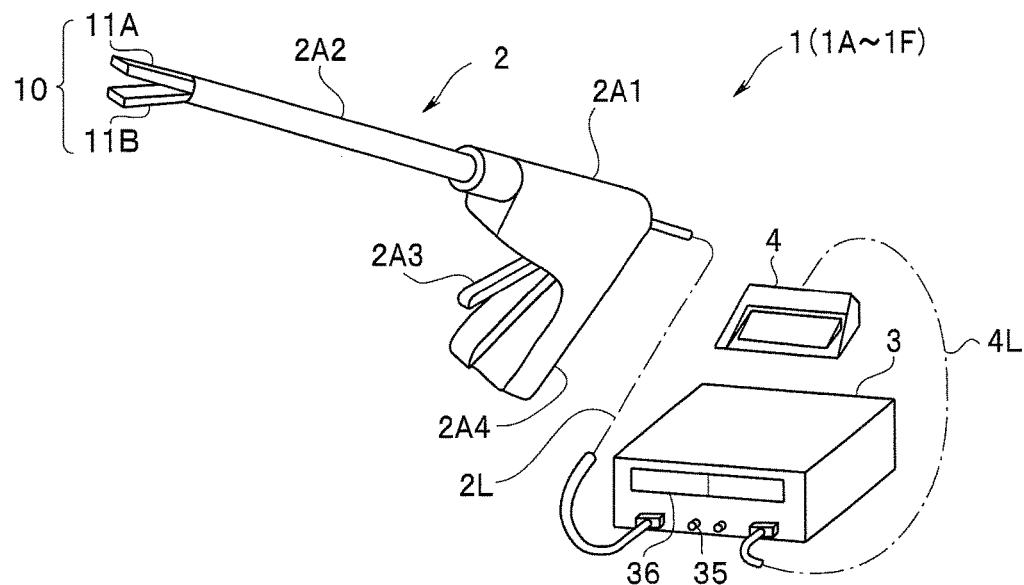
FIG. 1 is an external view of a living tissue bonding system of a first embodiment.

As illustrated in FIG. 1, a living tissue bonding system 1 of the present embodiment includes a treatment instrument 2, a body section 3 which is a treatment instrument control apparatus, and a foot switch 4. The treatment instrument 2 is a surgical energy anastomosis device that performs joining treatment or the like of living tissue inside an abdominal cavity through an abdominal wall for example.

The treatment instrument 2 includes a grip 2A1, a shaft 2A2, and a treatment section 10 composed of an openable and closable pair of clamping sections 11 (a first clamping section 11A and a second clamping section 11B) that holds and treats living tissue LT, which is a body to be treated.

Note that, hereinafter, when respective components of the same function for which A and B are imparted to ends of signs are expressed, the signs A and B are sometimes omitted. For example, the first clamping section 11A and the second clamping section 11B are respectively called the clamping sections 11.

The grip 2A1 is connected to the body section 3 through a cable 2L. The grip 2A1 with an opening/closing knob 2A3 with which an operator operates opening and closing of the treatment section 10 has a shape that the operator easily holds, a roughly L shape for example. At one end of the grip 2A1, the shaft 2A2 that is integrated with the treatment section 10 and transmits an operation of the opening/closing knob 2A3 to the treatment section 10 is disposed. On the other hand, the other end side of the grip 2A1 is a grasping section 2A4 to be grasped by the operator.

The body section 3 has a display section 36 that displays a treatment condition or the like and a setting operation section 35 with which the operator sets the treatment condition or the like on a front surface panel, and the foot switch 4 is connected through a cable 4L. By the operator pressurizing a pedal of the foot switch 4 with a foot, power output from the body section 3 to the treatment instrument 2 is ON/OFF controlled. The foot switch 4 is not an essential component, and may be a switch that the operator operates at hand or the like.

Figure 2A:
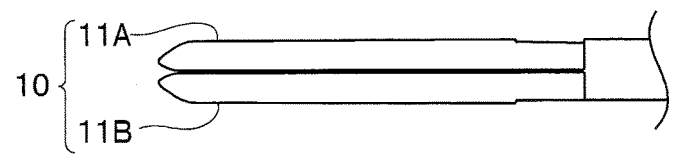
FIG. 2A is a side view of a treatment section of the living tissue bonding system of the first embodiment.
Figure 2B:
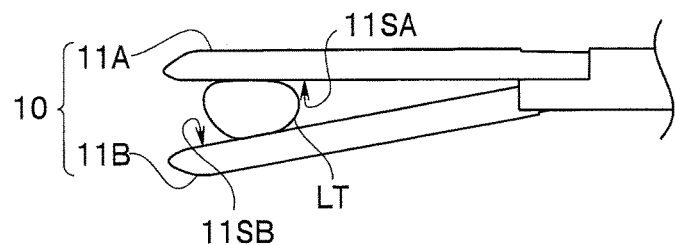
FIG. 2B is a side view of the treatment section of the living tissue bonding system of the first embodiment.

As illustrated in FIG. 2A and FIG. 2B, the treatment instrument 2 applies thermal energy (TH energy) to the living tissue LT through treatment surfaces 11S (11SA, 11SB) which are contact surfaces with the living tissue LT.

The treatment section 10 is freely openable and closable by the second clamping section 11B moving relative to the first clamping section 11A, for example. As illustrated in FIG. 2A, when the opening/closing knob 2A3 is not pressurized by the operator, the second clamping section 11B is in a close state or a contact state with the first clamping section 11A by energizing force of an elastic member not shown in the figure. In contrast, as illustrated in FIG. 2B, when the opening/closing knob 2A3 is pressurized by the operator with force stronger than the energizing force of the elastic member, the second clamping section 11B is separated from the first clamping section 11A and the treatment section 10 is turned to an open state. The living tissue LT inserted between the first clamping section 11A and the second clamping section 11B when the treatment section 10 is in the open state is, when the operator stops a pressurizing operation of the opening/closing knob 2A3, held in a state of being held and pressurized between the treatment surface 11SA of the first clamping section 11A and the treatment surface 11SB of the second clamping section 11B by the energizing force of the elastic member.

Figure 3A:
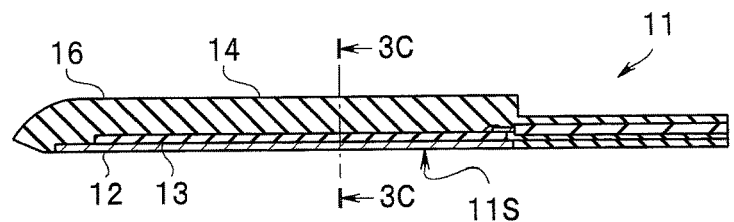
FIG. 3A is a sectional view of the treatment section of the living tissue bonding system of the first embodiment.
Figure 3B:
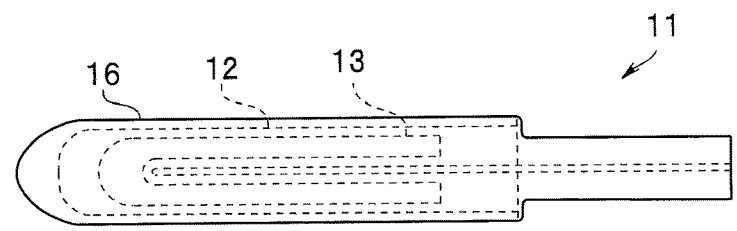
FIG. 3B is a top view of the treatment section of the living tissue bonding system of the first embodiment.
Figure 3C:
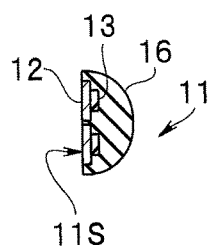
FIG. 3C is a sectional view along a 3C-3C line in FIG. 3A of the treatment section of the living tissue bonding system of the first embodiment.
Figure 4:
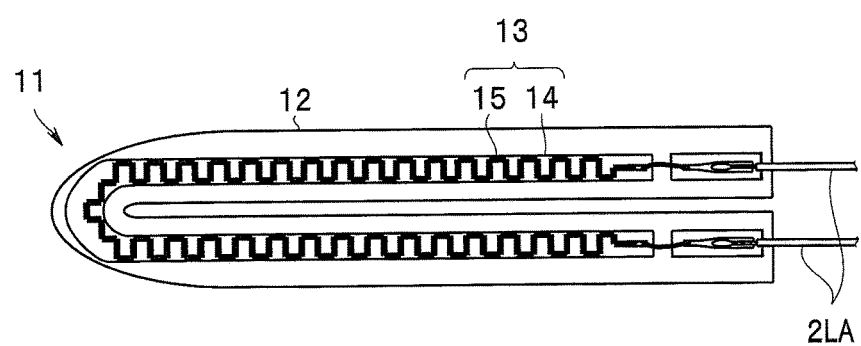
FIG. 4 is a top view of a heat generating section of the living tissue bonding system of the first embodiment.

As illustrated in FIG. 3A-FIG. 4, the treatment surface 11S of the clamping sections 11 is a front surface (outer surface) of a heat transfer body 12 composed of a metal such as stainless steel or copper. Then, to a back surface (inner surface) of the heat transfer body 12, a heating element 13 is bonded. An upper surface of the heating element 13 is covered with an insulator 16 such as polyimide, and insulated.

For the heating element 13, a heating resistor 15 is formed on a surface of a substrate 14 of alumina, aluminum nitride, or the like. The heating resistor 15 is composed of platinum of a positive temperature coefficient of resistance whose electric resistance R becomes high when a temperature rises. Therefore, as described later, an element temperature measuring section 39 can calculate a temperature T1 of the heating element 13 (heating resistor 15) from the electric resistance R of the heating resistor 15. For a material of the heating resistor 15, various kinds of high melting point metal materials of the positive temperature coefficient of resistance such as a NiCr alloy, Ta or W may be also used.

The heating element 13 is an output section that applies heat generation power (TH) outputted from the body section 3 to the living tissue LT as the thermal energy.

The heating element 13 is disposed to the respective clamping sections 11A and 11B, however, the heating element 13 may be disposed to at least one clamping section 11.

Figure 5:
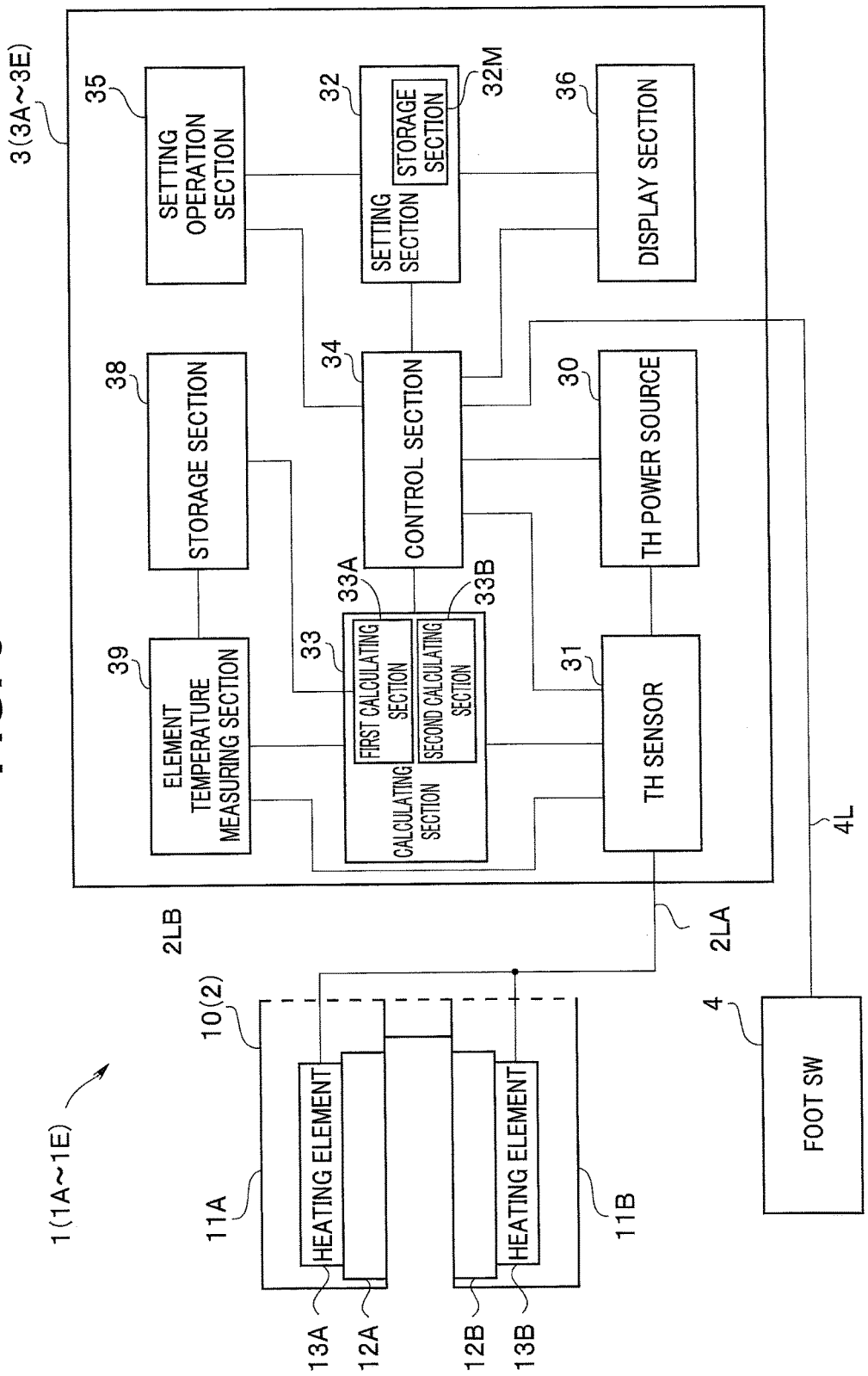
FIG. 5 is a block diagram of the living tissue bonding system of the first embodiment.

Next, a configuration of the living tissue bonding system 1 is described using FIG. 5. As already described, the living tissue bonding system 1 includes the treatment instrument 2, the body section 3 and the foot switch 4.

The body section 3 is provided with a heat generation power (TH) source 30, a heat generation power sensor (TH sensor) 31, a setting section 32, a calculating section 33, a control section 34, a storage section 38, and the element temperature measuring section 39.

The power source 30 outputs the heat generation power (TH) for the thermal energy. The TH sensor 31 which is a detecting section detects an output value (voltage and current) of TH. A product of the voltage and the current is power P.

The control section 34 controls the entire living tissue bonding system 1.

The element temperature measuring section 39 which is a temperature measuring section configured to measure a temperature of the output section indirectly measures an element temperature T1 by calculating the electric resistance R of the heating element 13 from the voltage and the current of TH and calculating the temperature (element temperature) T1 of the heating element 13 which is the output section from the calculated electric resistance R. That is, the element temperature measuring section 39 has a storage section (not shown in the figure) storing a calculating equation based on the temperature coefficient of resistance of the heating element 13 or a correspondence table of the electric resistance R and the element temperature T1 or the like. Note that the element temperature measuring section 39 may not calculate the electric resistance R from the voltage and the current of TH and may directly calculate the element temperature T1. Also, the element temperature measuring section 39 may directly measure the element temperature T1 by a temperature sensor such as a thermocouple disposed near the heating element 13.

Figure 6:
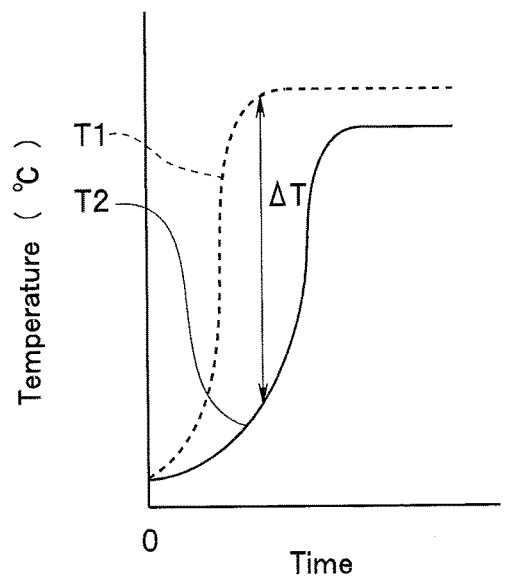
FIG. 6 is a graph for describing a change of a tissue temperature and a change of an element temperature in the living tissue bonding system of the first embodiment.

As illustrated in FIG. 6, there is a temperature difference $\Delta T$ between the element temperature T1 and a temperature (tissue temperature) T2 of the living tissue. Then, the temperature difference $\Delta T$ changes with a lapse of a treatment time period. Therefore, there is a case that it is not easy to perform appropriate treatment by control based on the element temperature T1.

Figure 7:
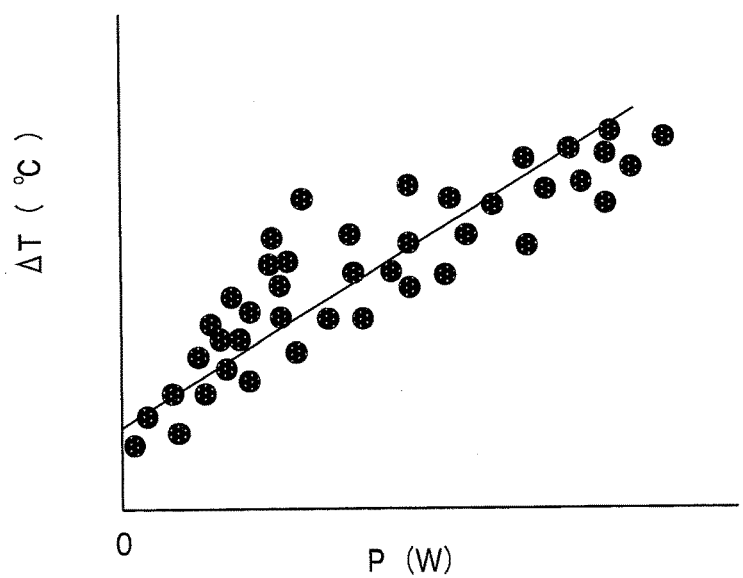
FIG. 7 is a graph illustrating a relation between a temperature difference between the tissue temperature and the element temperature and an output value of power, in the living tissue bonding system of the first embodiment.

An inventor has found, as a result of intensive studies, that the temperature difference $\Delta T$ is strongly correlated with an output value P of the heat generation power (TH), as illustrated in FIG. 7. This is because that, since the output value P is subjected to constant temperature control such that the element temperature T1 becomes a predetermined element temperature setting value Tset, when the temperature difference $\Delta T$ is large, TH of a larger output value P is needed.

Then, in the living tissue bonding system 1, in the storage section 38, a table (table data) or an equation for estimating the temperature difference $\Delta T$ between the element temperature T1 and the temperature T2 of the living tissue based on the output value of the power source 30 is stored.

Therefore, T2 can be calculated from a following (Equation 1).

$$T2=T1-\Delta T=T1-f(P) \quad \text{(Equation 1)}$$

Note that FIG. 7 illustrates a straight line for which a plurality of pieces of experimental data (plots) based on $\Delta T$ obtained by actually measuring the temperature of the living tissue using a temperature sensor are subjected to linear expression approximation by a least-squares method.

That is, an equation f(P) of a straight line illustrated in FIG. 6 is $\Delta T=\alpha P+\beta$ ($\alpha$: inclination, $\beta$: Y-intercept). The equation f(P) may be a quadratic equation or the like, or the power P may be sectioned into a plurality of ranges and the equation f(P) may be configured from a plurality of different equations for respective sections. Also, in the case of storing the table, $\Delta T$ corresponding to 5 W each of the power P for example is stored in the table.

Depending on kinds of the living tissue or the like, the different equation f(P) may be stored. Note that the tissue temperature T2 is not limited to an internal temperature of the living tissue, and may be a temperature of a surface in contact with the treatment surface 11S.

The calculating section 33 calculates the temperature T2 of the living tissue that is being treated. Hereinafter, for convenience of description, the calculating section 33 is separated into a first calculating section 33A and a second calculating section 33B by the functions and described.

The first calculating section 33A estimates the temperature difference $\Delta T$ using the stored table or equation stored beforehand based on the output value P of the power source 30.

The second calculating section 33B estimates the tissue temperature T2 using the (Equation 1) from the element temperature T1 measured by the element temperature measuring section 39 and the temperature difference $\Delta T$ estimated by the first calculating section 33A.

The setting section 32 sets the treatment condition based on an operation of the setting operation section 35 or the like. In the living tissue bonding system 1, the setting section 32 includes a storage section 32M. The storage section 32M composed of a semiconductor memory or the like may store the plurality of treatment conditions according to the kinds of the living tissue, for example. Note that the setting operation section 35 can be considered as a part of a setting section 32S in a broad sense.

A CPU or the like configuring the control section 34 may include at least some of functions of the element temperature measuring section 39, the calculating section 33 and the setting section 32. Also, the respective sections may be independent CPUs. Also, the storage section 38 composed of the semiconductor memory or the like may include the functions of the storage section 32M of the setting section and the storage section of the calculating section 33. Conversely, the calculating section 33 may include the semiconductor memory or the like having the function of the storage section 38.

The display section 36 is a notifying section that notifies the operator of information or the like such as the set treatment conditions, the output value of the power during treatment, and the tissue temperature T2.

In the living tissue bonding system 1, the control section 34 controls the power source 30 based on the tissue temperature T2 estimated by the second calculating section 33B.

<Operation Method of Living Tissue Bonding System>

Figure 8:
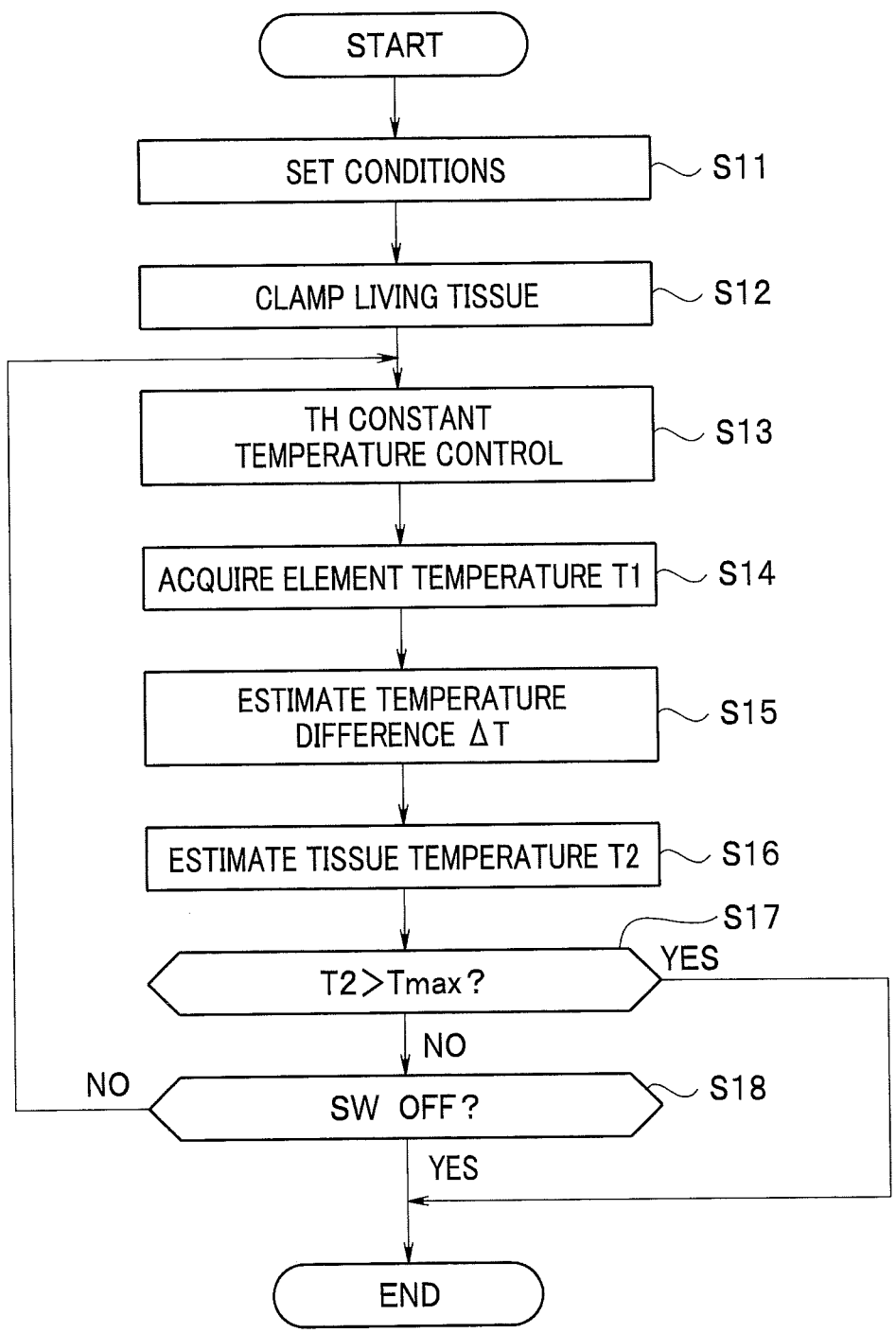
FIG. 8 is a flowchart for describing an operation method of the living tissue bonding system of the first embodiment.

Next, along a flowchart in FIG. 8, an operation method of the living tissue bonding system 1 is described.

<Step S11>

For example, the treatment conditions as follows are set through the setting section 32 including the setting operation section 35.

Tissue temperature setting value Tset: 190° C.
Upper limit temperature Tmax: 200° C.
Treatment time period t: 10 seconds Here, the tissue temperature setting value Tset is a target temperature for which the control section 34 performs constant temperature control. The upper limit temperature Tmax is a temperature at which a risk that the living tissue that is being treated is unexpectedly damaged and a peripheral portion is adversely affected starts to arise.

As already described, while the element temperature T1 is set as a target temperature for which the constant temperature control is performed in a conventional living tissue bonding system, in the living tissue bonding system 1, the tissue temperature T2 is set.

<Step S12>

As illustrated in FIG. 2A, the treatment section 10 in the closed state is inserted into an abdominal cavity through an abdominal wall, for example. When the operator performs a pressurizing operation of grasping the opening/closing knob 2A3 of the grip 2A1, the second clamping section 11B opens from the first clamping section 11A. Then, the living tissue LT which is a treatment target is arranged between the treatment surface 11SA of the first clamping section 11A and the treatment surface 11SB of the second clamping section 11B. In the state, when the opening/closing knob 2A3 is opened, by the energizing force of the elastic member, the second clamping section 11B is closed to the first clamping section 11A, and as illustrated in FIG. 2B, the living tissue LT which is the treatment target is clamped in a pressurized state between the treatment surface 11SA of the first clamping section 11A and the treatment surface 11SB of the second clamping section 11B.

<Step S13>

The operator pressurizes the foot switch 4 with a foot. Then, the control section 34 performs control such that the TH power source 30 outputs the heat generation power (TH).

<Step S14>

The element temperature measuring section 39 calculates the electric resistance R of the heating element 13 from the output value P (voltage and current) of the heat generation power, and calculates the temperature (element temperature) T1 of the heating element from the calculated electric resistance R.

In the living tissue bonding system 1, an average temperature of the heating elements 13A and 13B or the temperature of one of the heating elements 13A and 13B is considered as the element temperature T1 and the element temperature T1 is calculated.

<Step S15>

The first calculating section 33A estimates the temperature difference ΔT using the table or the equation stored beforehand based on the output value P.

<Step S16>

The second calculating section 33B estimates the tissue temperature T2 using the (Equation 1) from the element temperature T1 measured by the element temperature measuring section 39 and the temperature difference ΔT estimated by the first calculating section 33A.

<Step S17>

The control section 34 stops the treatment in the case that the tissue temperature T2 exceeds the upper limit temperature Tmax. At the time, it is preferable that the control section 34 displays an alarm at the display section 36.

<Step 18>

The control section 34 stops the treatment when pressurization of the foot switch 4 becomes absent (SW OFF: Yes). Until then, the treatment from step S13 is repeatedly performed.

In the living tissue bonding system 1, the body section 3 (treatment instrument control apparatus) and the operation method of the living tissue bonding system 1, the control is performed based on the temperature T2 of the living tissue that is being actually treated. Therefore, the tissue temperature T2 does not exceed the upper limit temperature Tmax. Also, more appropriate treatment can be performed compared to a conventional living tissue bonding system or the like in which the control is performed by the element temperature or the like.

Modifications of First Embodiment

Next, living tissue bonding systems 1A-1C, the treatment instrument control apparatus, and the operation method of the living tissue bonding system of modifications 1-3 of the first embodiment are described. Note that, hereinafter, "the living tissue bonding system, the treatment instrument control apparatus, and the operation method of the living tissue bonding system 1" are called the living tissue bonding system and the like. Since the living tissue bonding systems 1A-1C and the like are similar to the living tissue bonding system 1 and the like, same signs are attached to components of the same function and the description is omitted.

In the living tissue bonding system 1, the treatment energy to be applied is the thermal energy. However, as long as the treatment energy is the energy which is one of the thermal energy, ultrasound energy, light energy and high frequency power energy, similar effects can be obtained.

<Modification 1>

In the living tissue bonding system 1A and the like of the modification 1, a laser beam which is the light energy is applied to the living tissue as the treatment energy. That is, the power source outputs the power to a light source which generates the laser beam.

The living tissue to which the laser beam is applied generates heat. By selecting a wavelength of the laser beam, a specific treatment portion may be selectively heated.

<Modification 2>

In the living tissue bonding system 1B and the like of the modification 2, the ultrasound energy is applied to the living tissue as the treatment energy. That is, the power source outputs the power to an ultrasound transducer.

The treatment instrument of the living tissue bonding system 1B includes an ultrasound transducer inside the grip 2A1, and the clamping section 11A vibrates to produce ultrasound. The living tissue clamped with the fixed clamping section 11B generates heat by frictional heat.

<Modification 3>

In the living tissue bonding system 1C and the like of the modification 3, the high frequency power energy is applied to the living tissue as the treatment energy. That is, the power source outputs high frequency power.

A heat transfer body composed of a metal of the treatment instrument of the living tissue bonding system 1C has a function as an electrode that applies the high frequency power (HF) to the living tissue. When the high frequency power is applied to the living tissue LT clamped by electrodes 12A and 12B, the living tissue LT is heated by Joule heat.

In all of the living tissue bonding systems 1A-1C, the treatment instrument control apparatus, and the operation method of the living tissue bonding system of the modifications of the first embodiment, similarly to the living tissue bonding system 1 and the like, the temperature T1 of the output section and the output value P of the power source are measured, the temperature difference ΔT is estimated from the temperature T1 and the output value P, and the tissue temperature T2 is estimated from the temperature difference ΔT.

Then, in the case that the tissue temperature T2 exceeds the upper limit temperature Tmax, the treatment is stopped.

That is, the control section 34 controls the power source 30 such that the tissue temperature T2 estimated by the second calculating section 33B does not exceed the upper limit temperature Tmax. Therefore, in all of the living tissue bonding systems 1A-1C and the like of the modifications, it is easy to perform the appropriate treatment.

Second Embodiment

Next, a living tissue bonding system 1D and the like of the second embodiment are described. Since the living tissue bonding system 1D and the like are similar to the living tissue bonding system 1 and the like, the same signs are attached to the components of the same function and the description is omitted.

In the living tissue bonding system 1D, for example, the storage section 38 of a treatment instrument control apparatus 3D stores a table or an expression for estimating the temperature difference ΔT based not only on the output value P of the power source 30 but also on the output value P and the temperature T1 of the output section (heating element 13), and the first calculating section 33A estimates the temperature difference ΔT based on the output value P of the power and the temperature T1 of the output section.

That is, in the living tissue bonding system 1D, the first calculating section 33A calculates the temperature difference ΔT from the element temperature T1 of the heating element 13 and the output value P of the heat generation power (TH), in step S15 illustrated in FIG. 8.

As already described, the temperature difference ΔT between the tissue temperature T2 and the element temperature T1 is strongly correlated with the output value P of the heat generation power (TH). Then, by considering not only the output value P but also the element temperature T1, the temperature difference ΔT can be more accurately estimated.

$$\Delta T = f(P, T1) \qquad \text{(Equation 2)}$$

Figure 9:
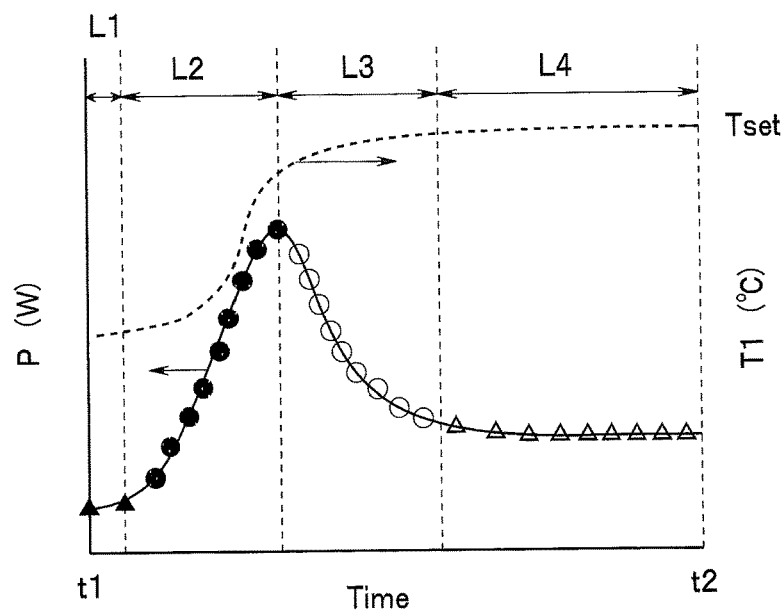
FIG. 9 is a graph illustrating a temporal change of an output value of heat generation power and a treatment section temperature, in a living tissue bonding system of a second embodiment.

As illustrated in FIG. 9, immediately after heating treatment is started (in an initial period L1), because of a heat capacity or the like of the heating element 13 itself, the element temperature T1 rises extremely slowly so that it can be considered as being roughly fixed. In contrast, while the temperature of the heating element 13 is rising (in a temperature rising period L2), the element temperature T1 is in a state of being greatly lower than the temperature setting value Tset. Therefore, the output value P suddenly increases. Then, when the element temperature T1 approaches the temperature setting value Tset (in a temperature rising completing period L3), the output value P starts to decrease in order to prevent overshoot. Then, when a stable state is attained, the output value P further decreases and becomes a roughly fixed value (a stable period L4).

Figure 10:
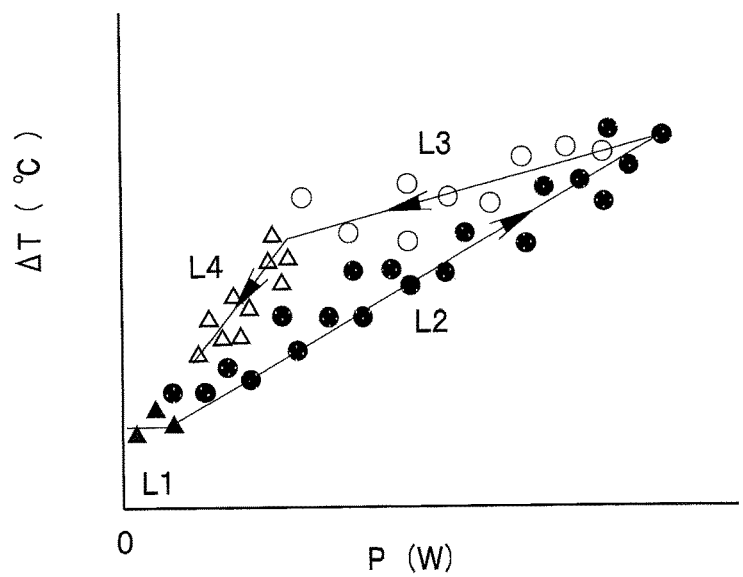
FIG. 10 is a graph illustrating a relation between a temperature difference between a living tissue temperature and the treatment section temperature and the output value of the heat generation power, in the living tissue bonding system of the second embodiment.

In FIG. 10, a relation between the output value P and the temperature difference ΔT is plotted separately in the four periods described above. That is, data of the period L1 is plotted with black triangle marks, data of the period L2 is plotted with black round marks, data of the period L3 is plotted with white round marks, and data of the period L4 is plotted with white triangle marks, respectively.

As is clear from FIG. 10, in the case of calculating the temperature difference ΔT from the output value P, by changing the calculating equation according to the four periods, calculation with higher accuracy is possible. Here, the first calculating section 33A determines the four periods L1-L4 from the element temperature T1 or the output value P.

That is, the time period immediately after the rising of the element temperature T1 is started is the period L1, the time period during the rising is the period L2, the time period during which the element temperature T1 approaches the element temperature setting value Tset, the output value P decreases and a decrease speed becomes equal to or lower than a predetermined value is the period L3, and the time period thereafter is the period L4.

The calculating equations in the respective periods can be appropriately set. For example, ΔT may be considered as being fixed in the period 1, and linear expression approximation may be performed in the periods L2-L4. Also, separation may be performed into five or more periods, or separation may be performed into three or fewer periods.

In the living tissue bonding system 1D and the like, since the temperature difference ΔT which is more highly accurate than that of a living tissue bonding system 1 and the like can be estimated, more appropriate treatment can be performed.

Note that the temperature difference ΔT is sometimes affected by pressurizing power PP between the treatment surface 11SA of the first clamping section 11A and the treatment surface 11SB of the second clamping section 11B. Therefore, by disposing a pressure sensor to the treatment surfaces 11S and using the pressurizing power PP also in estimation of the temperature difference ΔT, the more highly accurate temperature difference ΔT can be estimated. Note that the temperature difference ΔT is fixed with the pressurizing power PP equal to or greater than a predetermined pressure. Therefore, the control section 34 may control the power source 30 such that the treatment is not started in the case that the pressurizing power PP is below the predetermined pressure.

Third Embodiment

Next, a living tissue bonding system 1E and the like of the third embodiment are described. Since the living tissue bonding system 1E and the like are similar to the living tissue bonding system 1 and the like, the same signs are attached to the components of the same function and the description is omitted.

In the living tissue bonding system 1E, the calculating section 33 of a treatment instrument control apparatus 3E calculates a heating amount Q which is a time integrated value of the tissue temperature T2, and the control section 34 controls the power source 30 so as to reduce or end the output of the power when the heating amount Q becomes equal to or larger than a predetermined heating amount setting value Qset. That is, while treatment completion is controlled based on a preset treatment time period for example in the living tissue bonding system 1 and the like, the control is performed based on the heating amount Q in the living tissue bonding system 1E.

In order to obtain an excellent treatment result, it is needed to appropriately set an application time period of the treatment energy. Bonding strength is insufficient when the application time period is short, and surrounding tissue is adversely affected or the bonding strength becomes insufficient when the application time period is long.

Figure 11:
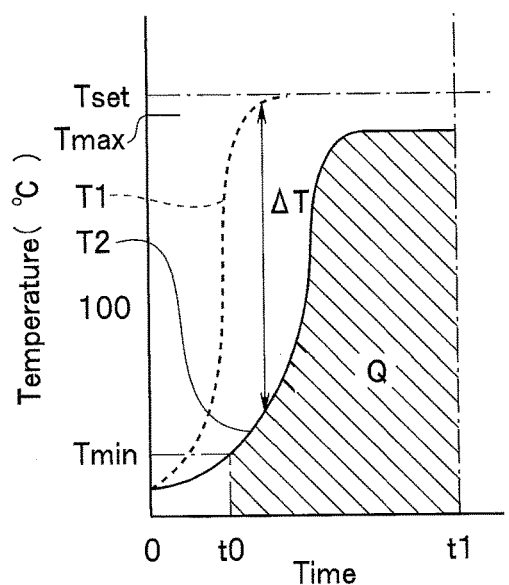
FIG. 11 is a graph for describing a heating amount, in a living tissue bonding system of a third embodiment.

The heating amount Q is the time integrated value of the temperature, that is, a product of the temperature and the application time period, and is indicated in units of "° C. second" for example. For example, by a following (Equation 3), the heating amount Q from treatment start (time 0) to the time t1 is calculated (see FIG. 11). Note that a lower limit temperature Tmin in FIG. 11 is described later.

$$Q = \int_0^{t1} T2 \, dt \quad \text{(Equation 3)}$$

The heating amount Q can be also expressed as an integrated value (integrated temperature) in units of "° C.", for which the living tissue temperature T2 at every predetermined interval of time, every second for example, is added. That is, the time integrated value of the temperature and the integrated temperature are physical quantities that are in different units but indicate the same state. Note that the heating amount Q is the physical quantity that is completely different from calories in units of joules.

Figure 12:
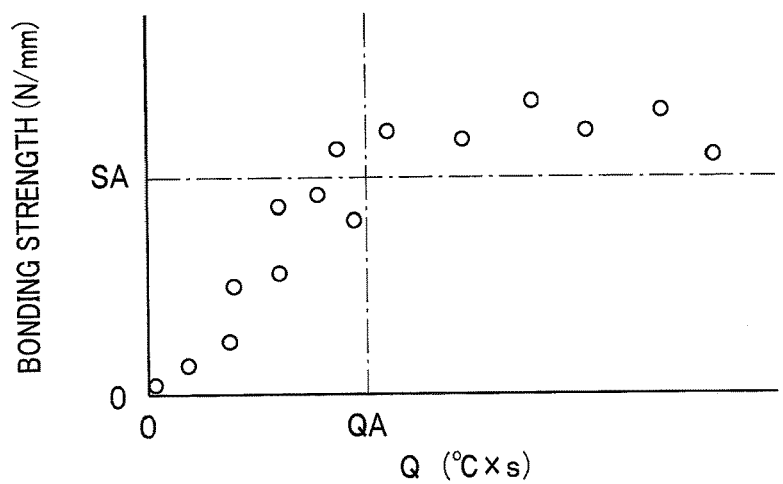
FIG. 12 is a graph illustrating a relation between the heating amount and living tissue bonding strength in the living tissue bonding system of the third embodiment.

FIG. 12 illustrates a relation between the heating amount Q and the bonding strength of the treated living tissue LT. From FIG. 12, it is clear that an excellent treatment result can be obtained by setting the heating amount Q as a standard. That is, when the heating amount Q is equal to or larger than a predetermined heating amount QA, practically, sufficient bonding strength SA can be obtained. For the heating amount QA, an experiment is conducted beforehand, and an obtained experimental value is stored in the storage section 32M.

<Operation Method of Living Tissue Bonding System>

Figure 13:
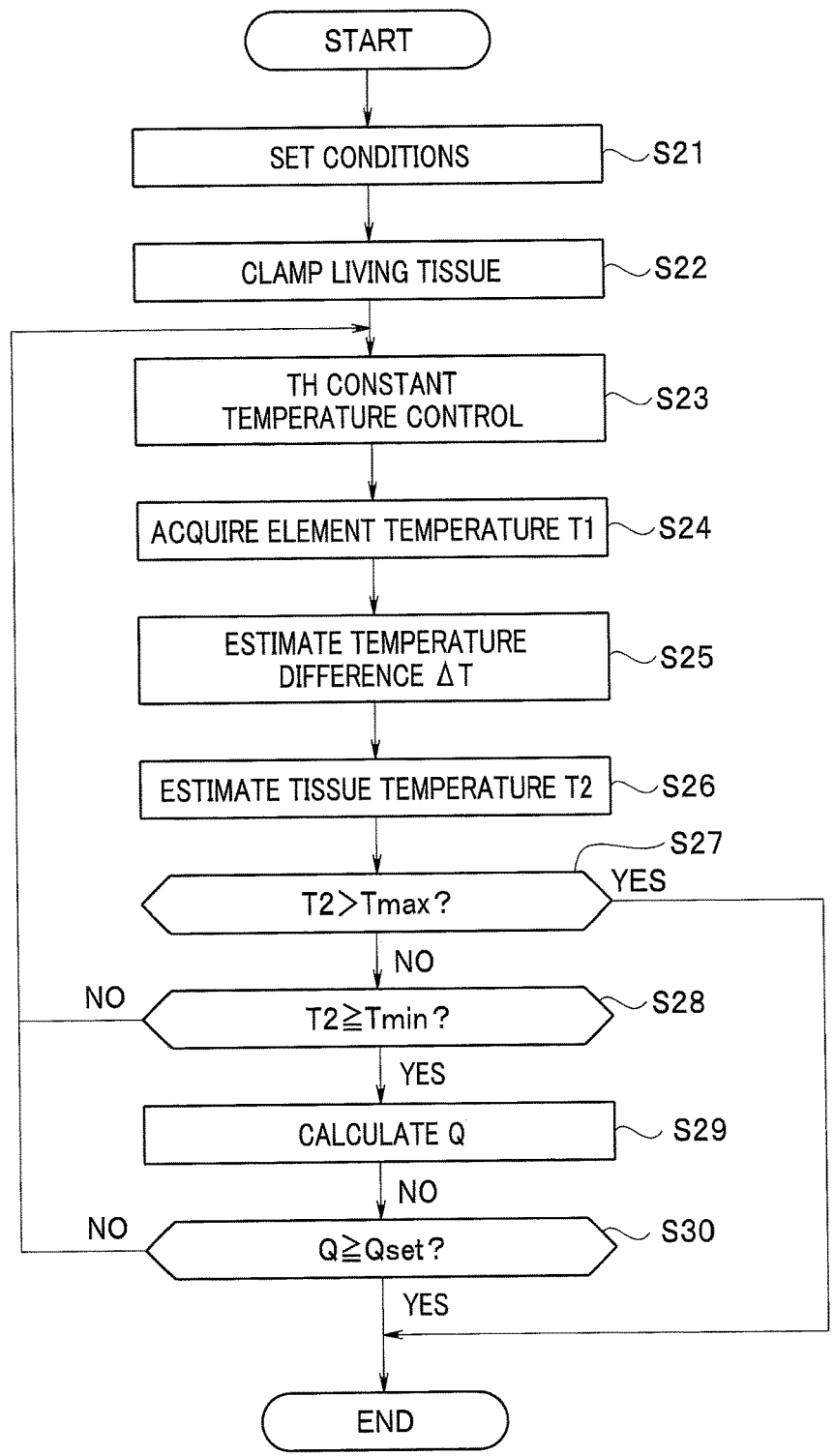
FIG. 13 is a flowchart for describing an operation method of the living tissue bonding system of the third embodiment.

Next, along a flowchart in FIG. 13, the operation method of the living tissue bonding system 1E is described.

<Step S21>

For example, the treatment conditions as follows are set through the setting section 32 including the setting operation section 35.

Tissue temperature setting value Tset: 220° C.
Heating amount setting value Qset: 800° C. second
Lower limit temperature Tmin: 50° C.
Upper limit temperature Tmax: 230° C.

Here, the lower limit temperature Tmin is the temperature at which the living tissue starts to change. In other words, the living tissue is not practically treated until the lower limit temperature Tmin.

As already described, while the treatment time period (the application time period of the treatment energy) is set as the treatment condition in the conventional living tissue bonding system, in the living tissue bonding system 1, the heating amount setting value Qset which is the time integrated value until the end of the application of the thermal energy of the tissue temperature T2 is set.

Note that the operator can set the treatment condition according to the treatment from the plurality of treatment conditions stored in the storage section 32M for example, however, as described later, the setting section 32 may automatically set it according to the kind of the living tissue LT.

That is, the respective conditions may be individually set, or may be selected as a treatment condition set in which the plurality of conditions are set beforehand. For example, a plurality of treatment condition sets LV1-LV3 may be stored in the storage section 32M beforehand according to the kind of the living tissue LT to be treated, as follows.

(LV1)
Tissue temperature setting value Tset: 180° C.
Heating amount setting value Qset: 1000° C. second
Lower limit temperature Tmin: 50° C.
Upper limit temperature Tmax: 190° C.

(LV2)
Tissue temperature setting value Tset: 190° C.
Heating amount setting value Qset: 2500° C. second
Lower limit temperature Tmin: 50° C.
Upper limit temperature Tmax: 200° C.

(LV3)
Tissue temperature setting value Tset: 200° C.
Heating amount setting value Qset: 3500° C. second
Lower limit temperature Tmin: 50° C.
Upper limit temperature Tmax: 210° C.

<Step S22-Step S27>

Since they are almost the same as step S12-step S17 illustrated in FIG. 8, the description is omitted.

<Step S28>

The control section 34 determines whether or not the tissue temperature T2 has risen to the lower limit temperature Tmin or higher. When it becomes the lower limit temperature Tmin or higher (YES), the process shifts to step S16. That is, the heating amount Q is not calculated while it is below the lower limit temperature Tmin (from the time 0 to t0).

<Step S29>

The calculating section 33 calculates the heating amount Q which is the time integrated value of the tissue temperature T2.

For the heating amount Q indicated by (Equation 3), at every predetermined interval of time, every second for example, ΔQ (tissue temperature T2×1 second) is added to the previous heating amount Q.

Note that, even when similar control is performed based on the heating amount which is the time integrated value of the element temperature T1 of the heating element 13, compared to conventional control based on time, an excellent treatment result can be obtained. However, in order to perform more accurate treatment, it is preferable to perform the control using the tissue temperature T2.

<Step S30>

When the heating amount Q becomes equal to or larger than the heating amount setting value Qset (YES), the control section 34 controls the TH power source 30, and ends the output of TH. That is, based on the heating amount setting value Qset and the heating amount Q, the output of TH is ended. Note that the control section 34 may control the TH power source 30 such that the output of TH decreases to a level at which there is practically no influence on the living tissue.

In the living tissue bonding system 1E, since the application time period of the thermal energy is controlled with the heating amount Q as the standard, an excellent treatment result can be easily obtained. That is, in the operation method of the living tissue bonding system 1E and the like, operability is excellent.

Also, it is preferable that a ratio Q/Qset of the heating amount Q calculated by the calculating section 33 to the heating amount setting value Qset is displayed at a notifying section 36B of the display section 36. For example, a state of treatment progress is displayed by a bar graph at the notifying section 36B. The operator can confirm a situation of the treatment progress by display at the notifying section 36B.

Note that notification of the ratio Q/Qset to the operator is not limited to the notifying section 36B of the display section 36 as long as it can be recognized by the operator, and the notifying section may perform notification by sound (sound information, a kind of a melody, a change of a frequency) or vibration strength or the like.

Fourth Embodiment

Next, a living tissue bonding system 1F and the like of the fourth embodiment are described. Since the living tissue bonding system 1F and the like are similar to the living tissue bonding system 1 or 1D and the like, the same signs are attached to the components of the same function and the description is omitted.

A treatment instrument 2F of the living tissue bonding system 1F applies the high frequency power energy (HF energy) and the thermal energy (TH energy) to the living tissue LT in order through the treatment surfaces 11SA and 11SB.

The HF energy has a function of releasing intracellular components including polymer compounds typified by protein by destroying cell membranes of the living tissue, and integrating the intracellular components with extracellular components typified by collagen. Also, the HF energy has a function of causing the temperature of the living tissue to rise. Then, by integration and temperature rise of the living tissue, dehydration treatment and bonding of the living tissue by the application of the thermal energy performed thereafter are accelerated.

Figure 14:
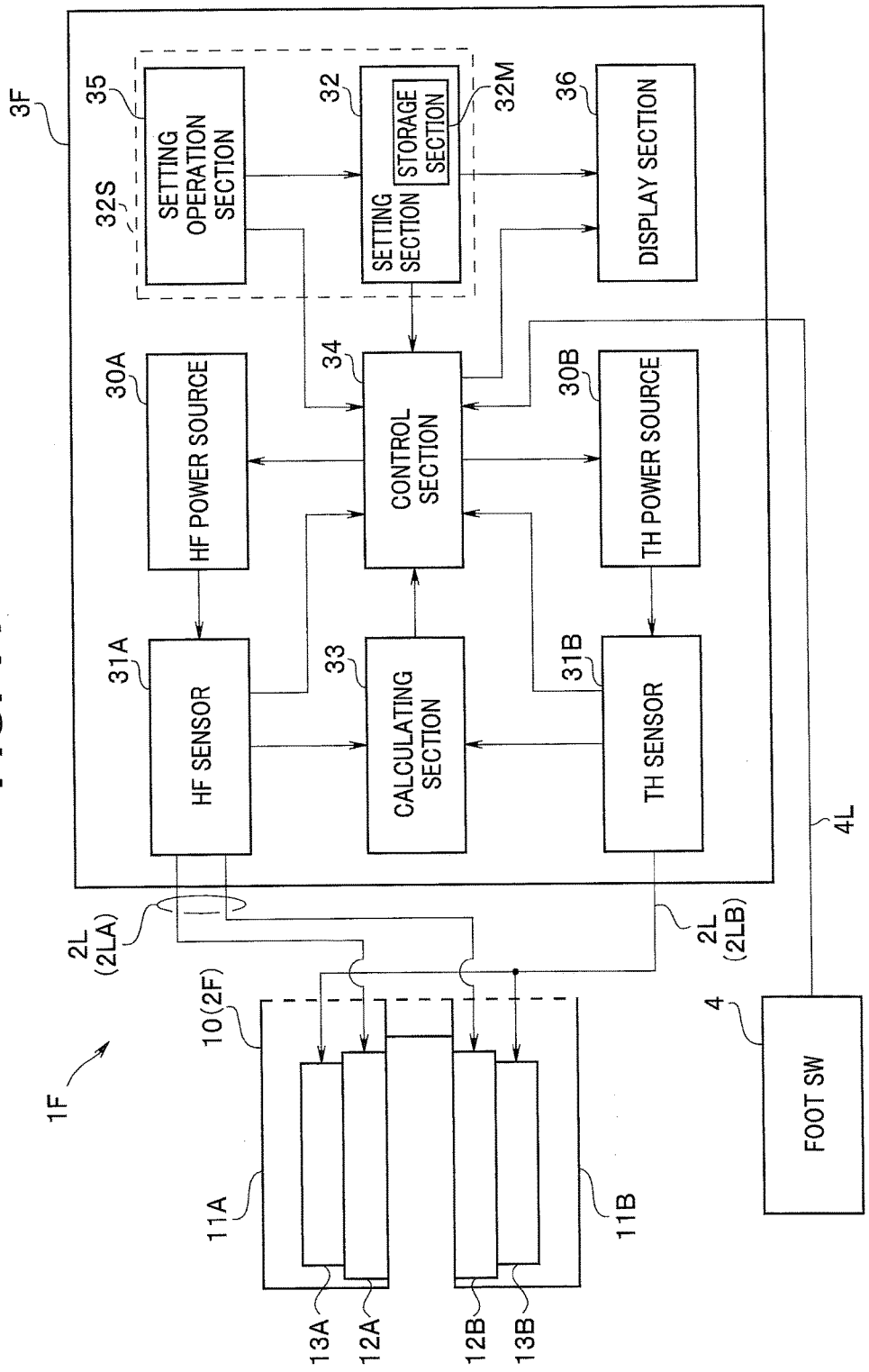
FIG. 14 is a block diagram of a living tissue bonding system of a fourth embodiment.

As illustrated in FIG. 14, a heat transfer body composed of a metal of the treatment instrument 2F of the living tissue bonding system 1F also has a function as an electrode 12. Then, a body section 3F which is the treatment instrument control apparatus includes a high frequency power (HF) source 30A which is a first power source, a heat generation power (TH) source 30B as a second power source, an HF sensor 31A, a TH sensor 31B, the setting section 32, the calculating section 33, and the control section 34.

The HF power source 30A outputs the high frequency power (HF) which is first power. The TH power source 30B outputs the heat generation power (TH) which is second power. Note that, since the HF power source 30A and the TH power source 30B do not simultaneously output the power, they may be one shared power source. In this case, the HF sensor 31A and the TH sensor 31B may be also shared.

The HF sensor 31A which is a first detecting section detects the output value (voltage and current) of HF. The TH sensor 31B which is a second detecting section detects the output value (voltage and current) of TH.

<Operation Method of Living Tissue Bonding System>

Figure 15:
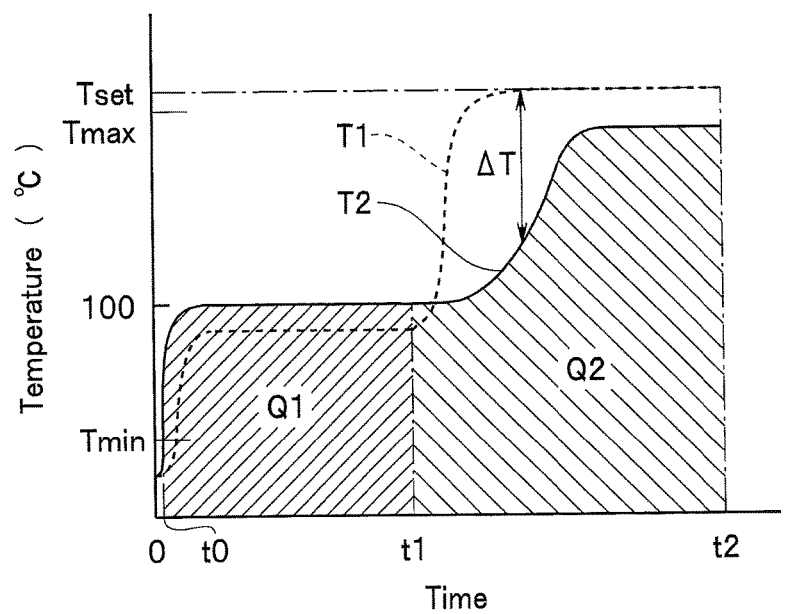
FIG. 15 is a graph for describing a temperature change of living tissue and a treatment section, and a heating amount in the living tissue bonding system of the fourth embodiment.

As illustrated in FIG. 15, in the living tissue bonding system 1F, after the application of the HF energy is ended, the application of the TH energy is started (time t=t1). Then, the control section 34 controls treatment end (time t=t2) based on the time integrated value of the tissue temperature T2 defined by the heating amount Q.

That is, when a total heating amount QT which is an added value of a high frequency power energy heating amount (first heating amount) Q1 by HF energy application and a thermal energy heating amount (second heating amount) Q2 by TH energy application becomes equal to or larger than the heating amount setting value Qset set beforehand (time t=t2), the control section 34 performs the control such that the TH power source 30B ends the TH energy application. That is, $$Qset \leq Q1 + Q2 \quad \text{(Expression 4)}$$

$$Q1 = \int_{t0}^{t1} T2\,dt$$

$$Q2 = \int_{t1}^{t2} T2\,dt$$

Figure 16:
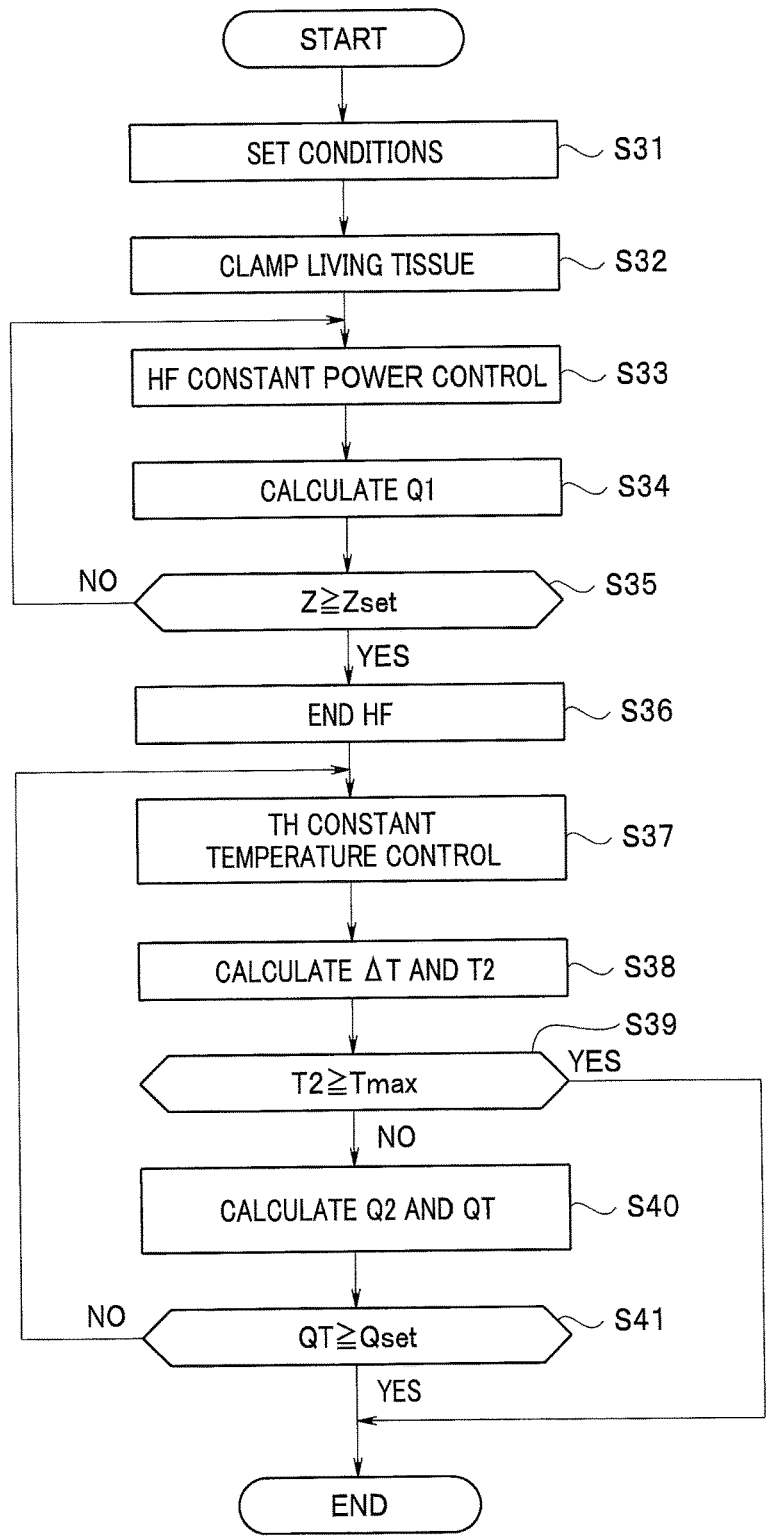
FIG. 16 is a flowchart for describing the operation method of the living tissue bonding system of the fourth embodiment.

Next, along a flowchart in FIG. 16, the operation method of the living tissue bonding system 1F is described in detail.

<Step S31>

For example, the treatment conditions as follows are set through the setting section 32 including the setting operation section 35.

HF output setting value Pset: 60 W

HF end impedance Zset: 120Ω

Element temperature setting value Tset: 180° C.

Heating amount setting value Qset: 1000° C. second

Note that the element temperature setting value Tset is set to exceed 70° C., to exceed 100° C. for example, which is higher than the tissue temperature (100° C.±30° C.) at the end of the HF application.

Also, similarly to the living tissue bonding system 1D and the like, the lower limit temperature Tmin and the upper limit temperature Tmax are also set, and the control section 34 performs the control based on the lower limit temperature Tmin and the upper limit temperature Tmax. However, since the control is the same as that in the living tissue bonding system 1D and the like, the description is omitted.

Note that the setting section 32 may automatically set the heating amount setting value Qset according to characteristics of the living tissue LT clamped by the pair of clamping sections 11.

For example, the heating amount setting value Qset is automatically set based on at least one of an interval G of the pair of clamping sections 11A and 11B by which the living tissue LT is clamped and initial impedance of HF.

The interval G is information on a size of the living tissue LT which is a body to be treated. The initial impedance of HF is tissue information including a moisture content of the living tissue LT. Also, as the initial impedance of HF, an impedance minimum value, or a time period during which impedance is equal to or smaller than a predetermined value, or the like can be used.

Further, when the operator selects an operative method by the setting operation section 35, the treatment conditions for a series of treatment are set by the setting section 32, and when treatment A is ended for example, the setting section 32 may automatically set the treatment condition for treatment B. For example, in the case that the operative method is "lung lobectomy", when (treatment A) lobar arteria sealing, (treatment B) lobar vein sealing, (treatment C) lobar bronchial sealing, and (treatment D) interlobar solid organ sealing are to be continuously performed in order, since the treatment conditions for a series of (treatment A)-(treatment D) are set just by the operator selecting the operative method, the operability is excellent.

<Step S32>

The living tissue LT which is the treatment target is clamped in the pressurized state between the treatment surface 11SA of the first clamping section 11A and the treatment surface 11SB of the second clamping section 11B.

<Step S33>

In the state that the living tissue LT is clamped at the treatment section 10, the operator pressurizes the foot switch 4 with a foot. Then, the control section 34 starts the treatment. That is, the control section 34 first performs the control such that the HF power source 30A outputs the high frequency power (HF). HF is transmitted through the cable 2L to the electrodes 12A and 12B of the treatment instrument 2. Then, the high frequency power is applied to the living tissue LT clamped by the electrodes 12A and 12B, and the living tissue LT is heated by Joule heat.

That is, the HF energy makes the living tissue itself present in an energizing route of HF between the electrode 12A and the electrode 12B generate heat. Therefore, in an HF energy applying process, even when the living tissue LT is thick, the tissue temperature T2 rises without generating temperature irregularities to a center portion. Note that, even though the treatment section 10 does not generate heat, the element temperature T1 also rises by heat transfer from the living tissue LT which generates heat.

The control section 34 performs constant power control to an output value P1 of HF by the HF output setting value Pset, 60 W for example, based on the current and the voltage of HF detected by the HF sensor 31A.

<Step S34>

The calculating section 33 measures the tissue temperature T2 by a temperature sensor 19 inserted to the living tissue LT, or an infrared ray sensor or the like, and calculates the high frequency power energy heating amount (first heating amount) Q1 which is the time integrated value (integrated value) of the tissue temperature T2.

Here, as illustrated in FIG. 15, the tissue temperature T2 when the HF energy is applied can be considered as being fixed since the living tissue LT contains water, after drastically increasing in an initial period. That is, even when the energy is applied, the temperature of the living tissue LT containing water is held at the temperature near a boiling point (100° C.) which is a fixed temperature under atmospheric pressure for example, at 100° C.±30° C. for example.

Therefore, the first heating amount Q1 after the treatment is started until the time t may be calculated by a following (Expression 5) without using a sensor or the like.

$$Q1 \approx T2 \times t \approx 100° C. \times t \quad \text{(Expression 5)}$$

Further, the first heating amount Q1 may be calculated (step S34) by the calculating section 33 using a following (Equation 6), after step S36 described later.

$$Q1 = 100° C. \times t1 \quad \text{(Equation 6)}$$

Provided that t1; HF energy application time

As described above, in S34, while the constant power control is performed to HF and the HF energy is applied, the tissue temperature T2 may be considered as a predetermined fixed temperature (100° C.) and the first heating amount Q1 which is the time integrated value may be calculated.

<Step S35>

In the living tissue bonding system 1F, when HF energy application is started, impedance Z is calculated by the calculating section 33 from the voltage and the current of HF detected by the HF sensor 31A.

By dehydration or the like accompanying degeneration of the living tissue LT accompanying progress of the treatment, the impedance Z rises. The control section 34 performs the treatment from S33 until the impedance Z becomes equal to or greater than the set HF end impedance Zset (No).

<Step S36>

When the impedance Z becomes equal to or greater than the set HF end impedance Zset (YES), in S36, the control section 34 controls the HF power source 30A and ends the output of HF (t=t1).

That is, based on the impedance Z of HF, the output of HF is ended.

<Step S37>

The control section 34 starts the control of applying the TH energy instead of the HF energy to the living tissue LT.

In the TH energy application, the control section 34 performs the constant temperature control on an output value P2 of the TH power source 30B based on the element temperature T1 of the treatment section 10. In other words, the heating element 13 is controlled so as to be the element temperature setting value Tset set in S31. TH may be a direct current or a high frequency, and a frequency in the case of the high frequency may be the same as HF.

Note that the control section 34 may perform the constant temperature control to the output value P2 of the TH power source 30B based on the tissue temperature T2, similarly to the living tissue bonding system 1 and the like.

While the high frequency power (HF) applied from the electrode 12 to the living tissue LT heats the living tissue LT as Joule heat, the heat generation power (TH) directly transfers the thermal energy to the living tissue LT. The thermal (TH) energy transferred to the living tissue LT through the treatment surfaces 11S can heat the tissue temperature T2 to the temperature exceeding 100° C., regardless of a degeneration state, the moisture content for example, of the living tissue LT, according to the element temperature setting value Tset.

<Step S38>

The calculating section 33 calculates the second heating amount (thermal energy heating amount) Q2 which is the time integrated value of the tissue temperature T2. That is, in S38, the element temperature measuring section 39 (not shown in the figure) calculates the element temperature T1 from the electric resistance R, performs the constant temperature control to TH based on the element temperature T1, and applies the thermal energy to the living tissue LT. Then, the first calculating section 33A estimates the temperature difference ΔT using a second table or a second equation stored in the storage section 38 (not shown in the figure), based on the output value of the power source 30B. The second table and the second equation are the table or the equation acquired beforehand based on an experiment, for estimating a temperature difference ΔT2 between a temperature T1B of the heating element to which the TH power is applied and the temperature (tissue temperature) T2 of the living tissue to which the TH energy is applied, based on the output value P2 of the TH power source.

\<Step S39>

The control section 34 stops the treatment in the case that the tissue temperature T2 exceeds the upper limit temperature Tmax.

\<Step S40>

The calculating section 33 calculates the second heating amount Q2 which is the time integrated value of the tissue temperature T2. Further, the calculating section 33 calculates the total heating amount QT for which the first heating amount Q1 and the second heating amount Q2 are added.

\<Step S41>

When the total heating amount QT becomes equal to or larger than the heating amount setting value Qset (YES), the control section 34 controls the TH power source 30B and ends the output of TH (t=t2). That is, based on the heating amount setting value Qset and the total heating amount QT, the output of TH is ended.

Here, since the first heating amount Q1 is already calculated and does not increase or decrease in the process after S36, the control section 34 may end the output of TH when a heating residual amount ΔQ indicated by a following (Equation 7) becomes zero.

Heating residual amount Δ$Q$=heating amount setting value $Q$set−first heating amount $Q$1−second heating amount $Q$2     (Equation 7)

Note that the control section 34 may calculate the total heating amount QT or the heating residual amount ΔQ. Also, the heating amount Q may be calculated only in a TH applying process without calculating the heating amount Q in an HF applying process.

In the living tissue bonding system 1F and the like, since the application time period of the energy, that is, energy application end, is controlled using the heating amount Q of the living tissue temperature T2, an excellent treatment result can be easily obtained. Therefore, the operability is excellent in the living tissue bonding system 1F and the like.

Note that, in the above description, a case that first energy applied first is the high frequency power energy and second energy applied next is the thermal energy is described. However, when the first energy is the energy which is one of the high frequency power energy, the thermal energy, the light energy and the ultrasound energy and the second energy is any one kind of the energy different from the first energy, similar effects can be obtained.

That is, a living tissue bonding system in which a treatment instrument applies two or more kinds of the treatment energy selected from the thermal energy, the ultrasound energy, the light energy and the high frequency power energy in order to the living tissue and a control section reduces or ends the output of at least one kind of the treatment energy based on the heating amount has the effects similar to that of the living tissue bonding system 1E.

For example, even a living tissue bonding system that stops bleeding of a blood vessel by the application of the HF energy and then cuts off the blood vessel by the application of the ultrasound energy has the similar effects by performing the control similar to that of the living tissue bonding system 1D.

Also, a bipolar treatment instrument with which the living tissue LT is grasped by the pair of clamping sections 11 is described; however, even with a monopolar treatment instrument, as long as the control is performed similarly with the total heating amount QT as a standard in the living tissue bonding system, an excellent treatment result can be easily obtained.

The present invention is not limited to the above-described embodiments and the like, and various changes and alterations and the like can be made within a range that does not depart from gist of the present invention.

What is claimed is:

1. A living tissue bonding system comprising:
    a clamping section configured to clamp living tissue;
    an output section provided on the clamping section and configured to output a treatment energy to the living tissue;
    a power source configured to output electric power to the output section for generating the treatment energy;
    a controller configured to perform constant temperature control to control the power source by setting a temperature of the output section as a predetermined setting value;
    a memory configured to store, in advance of treatment, a table or an equation for indicating a linear relationship between the electric power output by the power source and the temperature difference between a temperature of the living tissue and the temperature of the output section, the temperature of the living tissue and the temperature of the output section being measured in advance as a condition of the constant temperature control;
    a sensor configured to detect a current and a voltage outputted by the power source and calculate the electric power based on the detected current and the detected voltage;
    a processor being configured to perform the following steps:
        obtain an actual electric power output by the power source;
        determine the temperature difference between the temperature of the output section and the temperature of the living tissue based on the actual electric power output by the power source under the constant temperature control by using the table or the equation stored in the memory;
        calculate an electric resistance of the output section from the voltage and current of the electric power detected by the sensor, and calculate the temperature of the output section from the calculated electric resistance; and
        determine an estimated temperature of the living tissue by subtracting the determined temperature difference between the temperature of the output section and the temperature of the living tissue from the calculated temperature of the output section from the calculated electric resistance.

2. The living tissue bonding system according to claim 1, wherein the treatment energy is at least one of thermal energy, ultrasound energy, light energy, and high frequency power energy.

3. The living tissue bonding system according to claim 2, wherein the controller is configured to control the power source so that the estimated temperature of the living tissue does not exceed a predetermined upper limit temperature.

4. The living tissue bonding system according to claim 3, wherein:
    the treatment energy is the thermal energy;
    the output section is a heating element which converts the power to the thermal energy; and
    the heating element includes a heating resistor formed on a substrate.

5. The living tissue bonding system according to claim 4, wherein the controller is configured to control the power source so as to reduce or end output of the power when a heating amount which is a time integrated value of the estimated temperature of the living tissue, becomes equal to or larger than a predetermined heating amount setting value.

6. The living tissue bonding system according to claim 2, wherein the treatment instrument applies, to the living tissue, two or more kinds of the treatment energy selected from the thermal energy, the ultrasound energy, the light energy, and the high frequency power energy in order.

7. A treatment instrument control apparatus configured to control treatment energy outputted to an output section that is provided on a clamping section, the clamping section being configured to clamp living tissue, the treatment instrument control apparatus comprising:
a power source configured to output electric power to the output section for generating the treatment energy;
a controller configured to perform a constant temperature control to control the power source by setting a temperature of the output section as a predetermined setting value;
a memory configured to store, in advance of treatment, a table or an equation for indicating a linear relationship between the electric power output by the power source and the temperature difference between a temperature of the living tissue and the temperature of the output section, the temperature of the living tissue and the temperature of the output section being measured in advance as a condition of the constant temperature control;
a sensor configured to detect a current and a voltage outputted by the power source and calculate the electric power based on the detected current and the detected voltage;
a processor configured to perform the following steps:
obtain an actual electric power output by the power source;
determine the temperature difference between the temperature of the output section and the measured temperature of the living tissue based on the actual electric power output by the power source under the constant temperature control by using the table or equation stored in the memory;
calculate an electric resistance of the output section from the voltage and current of the electric power detected by the sensor, and calculate the temperature of the output section from the calculated electric resistance; and
determine an estimated temperature of the living tissue by subtracting the determined temperature difference between the temperature of the output section and the temperature of the living tissue from the calculated temperature of the output section from the calculated electric resistance.

8. An operation method of a living tissue bonding system comprising:
outputting treatment energy with an output section provided on a clamping section, the treatment energy being electric energy from a power source for bonding living tissue clamped by the clamping section;
performing a constant temperature control to control the power source by setting a temperature of the output section as a predetermined setting value;
storing, in advance of treatment, a table or an equation in a memory for indicating a linear relationship between the electric power output by the power source and the temperature difference between a temperature of the living tissue and the temperature of the output section, the temperature of the living tissue and the temperature of the output section being measured in advance as a condition of the constant temperature control;
detecting a current and a voltage outputted by the power source and calculating the electric power based on the detected current and the detected voltage;
obtaining an actual electric power output by the power source;
determining the temperature difference between the temperature of the output section and the temperature of the living tissue based on the electric power output by the power source under the constant temperature control by using the stored table or the equation;
calculating an electric resistance of the output section from the voltage and current of the electric power detected by the sensor, and calculates the temperature of the output section from the calculated electric resistance; and
determining an estimated temperature of the living tissue by subtracting the determined temperature difference between the temperature of the output section and the temperature of the living tissue from the calculated temperature of the output section from the calculated electric resistance.

9. The operation method of the living tissue bonding system according to claim 8, wherein the treatment energy is at least one of thermal energy, ultrasound energy, light energy, and high frequency power energy.

10. The operation method of the living tissue bonding system according to claim 9, further comprising the step of controlling the power source so that the final estimated temperature of the living tissue estimated does not exceed a predetermined upper limit temperature.

11. The operation method of the living tissue bonding system according to claim 9, wherein:
the treatment energy is the thermal energy, and
the output section is a heating element which converts the power to the thermal energy.

12. The operation method of the living tissue bonding system according to claim 11, further comprising the step of controlling the power source so as to reduce or end output of the power when a heating amount which is a time integrated value of the estimated temperature of the living tissue becomes equal to or larger than a predetermined heating amount setting value.

13. The operation method of the living tissue bonding system according to claim 9, further comprising the step of applying, to the living tissue, two or more kinds of the treatment energy selected from the thermal energy, the ultrasound energy, the light energy, and the high frequency power energy in order.

14. The living tissue bonding system of claim 1 wherein:
the controller is configured to reduce or terminate the output of the electric power from the power source based on the estimated temperature of the living tissue.

* * * * *

UNITED STATES PATENT AND TRADEMARK OFFICE
CERTIFICATE OF CORRECTION

| | |
|---|---|
| PATENT NO. | : 10,342,596 B2 |
| APPLICATION NO. | : 14/979715 |
| DATED | : July 9, 2019 |
| INVENTOR(S) | : Yoshitaka Honda et al. |

Page 1 of 1

It is certified that error appears in the above-identified patent and that said Letters Patent is hereby corrected as shown below:

In the Claims

Column 19, Lines 1-4 should read:
-- source so as to reduce or end output of the power when a
heating amount, which is a time integrated value of the
estimated temperature of the living tissue, becomes equal to
or larger than a predetermined heating amount setting value. --

Column 20, Lines 46-49 should read:
-- 12. The operation method of the living tissue bonding
system according to claim 11, further comprising the step of
controlling the power source so as to reduce or end output
      of the power when a heating amount, which is a time --

Signed and Sealed this
Twelfth Day of November, 2019

Andrei Iancu
*Director of the United States Patent and Trademark Office*